United States Patent [19]

Eierdanz et al.

[11] Patent Number: 4,956,124

[45] Date of Patent: Sep. 11, 1990

[54] BICYCLIC DECANEDIOIC ACIDS, A PROCESS FOR THEIR PRODUCTION, AND THEIR USE AS FLOTATION AIDS

[75] Inventors: Horst Eierdanz, Hilden; Paul Schulz, Wuppertal; Wolfgang von Rybinski; Rita Koester, both of Duesseldorf, all of Fed. Rep. of Germany

[73] Assignee: Henkel Kommanditgesellschaft auf Aktien, Duesseldorf, Fed. Rep. of Germany

[21] Appl. No.: 193,304

[22] Filed: May 11, 1988

[30] Foreign Application Priority Data

May 11, 1987 [DE] Fed. Rep. of Germany ....... 3715613

[51] Int. Cl.$^5$ .................. B03C 1/02; C07C 61/13
[52] U.S. Cl. .................... 260/410; 562/502; 560/256; 568/665; 252/61; 209/166
[58] Field of Search ............. 562/502; 560/256; 568/665; 209/166, 167; 260/410; 252/61

[56] References Cited

U.S. PATENT DOCUMENTS

| | | | |
|---|---|---|---|
| 2,265,601 | 12/1941 | Imelmann | 274/38 |
| 2,323,861 | 7/1943 | Zellner | 260/533 |
| 2,394,582 | 2/1946 | Bruson | 260/611 |
| 2,395,452 | 2/1946 | Bruson | 260/497 |
| 3,065,192 | 11/1962 | Dimler | 260/410 |
| 3,278,580 | 10/1966 | Worsley | 260/410 |
| 3,287,395 | 11/1966 | Chang | 562/502 |
| 3,364,047 | 1/1968 | McGary | 260/410 |
| 3,646,113 | 2/1972 | Rick | 260/410 |
| 3,701,804 | 10/1972 | Knoth et al. | 260/530 |
| 3,786,068 | 1/1974 | Kelly | 562/502 |
| 4,144,244 | 3/1979 | Brace | 562/502 |
| 4,166,915 | 9/1979 | Buchholz | 562/502 |
| 4,331,608 | 5/1982 | Kawamoto et al. | 260/406 |

FOREIGN PATENT DOCUMENTS

| | | |
|---|---|---|
| 2035558 | 7/1970 | Fed. Rep. of Germany . |
| 2106307 | 2/1971 | Fed. Rep. of Germany . |
| 0981609 | 5/1951 | France . |
| 1068905 | 5/1967 | United Kingdom . |

OTHER PUBLICATIONS

Tetrahedron Letters (periodical)–No. 42, pp. 3685–3688, "Total Synthesis of (±)-trans-Sweroside Aglucone O-methyl ether", by Furuichi et al.
Chemical Abstracts, vol. 102, No. 13, Apr. 1, 1985, p. 691, No. 113268m.
Chemical Abstracts, vol. 102, No. 13, Apr. 1, 1985, p. 693, No. 113295t.
Polymers Paint Colour Journal, Europ. Suppl., 1985, p. 115.
Journal of the American Oil Chemists Society, 57, 219 (1975).
Brennstoff-Chemie, 50, 212 (1969).
Can. J. Chem., 33, 1914 (1955).
Journal of the American Oil Chemists Society, 54, 870A (1977).
Chemical Communications, 21, 1420 (1970).
F. D. Gunstone, Hydroxylation Methods, Advances in Org. Chem. Bd. I, Intersc. Publ., p. 103 ff, 1960.
Colloid & Polymer Sci., 259 (1981), pp. 775–776.

*Primary Examiner*—David L. Lacey
*Assistant Examiner*—Thomas M. Lithgow
*Attorney, Agent, or Firm*—Ernest G. Szoke; Wayne C. Jaeschke; Henry E. Millson, Jr.

[57] ABSTRACT

Bicyclic decanedioic acids corresponding to the following general formula

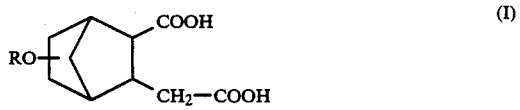

in which R represents a $C_1$–$C_{22}$ alkyl radical, a $C_2$–$C_{34}$ alkylcarbonyl radical, or a residue of a polyalkoxylated $C_2$–$C_{22}$ fatty alcohol, represent a new class of dicarboxylic acids which are useful as flotation aids in the flotation of non-sulfidic ores.

6 Claims, No Drawings

BICYCLIC DECANEDIOIC ACIDS, A PROCESS FOR THEIR PRODUCTION, AND THEIR USE AS FLOTATION AIDS

BACKGROUND OF THE INVENTION

1. Field of the Invention

This invention relates to bicyclic decanedioic acids, a process for their preparation, and their use as flotation aids in the flotation of nonsulfidic ores.

2. Statement of Related Art

Dicarboxylic acids based on fats, for example the so-called dimer acids, are important compounds for which the potential applications are numerous, cf. Polymers Paint Colour Journal, Europ. Supplement, 1985, 115. The favorable properties of this class of compounds are largely attributable to the presence of long alkyl chains. However, dicarboxylic acids containing more than 12 carbon atoms can only be prepared by a few reactions.

Thus, the dimerization of unsaturated $C_{18}$ fatty acids leads to the above-mentioned dimer acids containing 36 carbon atoms. The reaction of fatty acids with acrylic acid gives a $C_{21}$ dicarboxylic acid, cf. IAOCS 57, 219 (1975). The hydroxycarboxylation of unsaturated fatty acids gives $C_{19}$ dicarboxylic acids, cf. Fette, Seifen, Anstrichmittel 87, 400 (1985).

DESCRIPTION OF THE INVENTION

Other than in the operating examples, or where otherwise indicated, all numbers expressing quantities of ingredients or reaction conditions used herein are to be understood as modified in all instances by the term "about".

This invention relates to bicyclic decanedioic acids corresponding to the following general formula

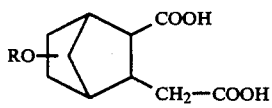
(I)

in which R is selected from:
(a) linear or branched, saturated $C_1$-$C_{22}$ alkyl radicals,
(b) linear or branched, saturated $C_2$-$C_{34}$ alkylcarbonyl radicals, and
(c) residues of polyalkoxylated fatty alcohols corresponding to the following formula

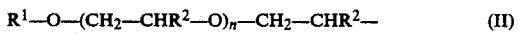

$$R^1-O-(CH_2-CHR^2-O)_n-CH_2-CHR^2- \quad (II)$$

in which $R^1$ is a saturated $C_2$-$C_{22}$ alkyl group from a fatty alcohol radical, $R^2$ is hydrogen and/or methyl and n is a number of from 0 to 24, preferably from 1 to 9.

It has now been found that it is possible by a simple reaction to synthesize the above group of new fat-based dicarboxylic acids corresponding to general formula (1) which show interesting properties, for example as intermediate products or as flotation aids, more especially as collectors for the flotation of non-sulfidic ores.

Starting materials for the decanedioic acids of the invention include dicyclopentadiene and linear or branched, saturated $C_1$-$C_{22}$ alcohols, for example methanol ethanol, n-propanol, i-propanol, n-butanol and isomers thereof, 2ethylhexanol, branched octanols and $C_8$-$C_{18}$ fatty alcohols, including those obtained in the form of technical mixtures from the synthesis of fatty alcohols. Decanedioic acids according to the invention containing an ether constituent are thereby obtained.

Alternatively, instead of the above alcohols, linear or branched, saturated $C_2$-$C_{34}$ fatty acids can also be reacted with dicyclopentadiene, including for example acetic acid, propionic acid, butyric acid, valeric acid, caproic acid, oenanthic acid, caprylic acid, pelargonic acid, capric acid, undecanoic acid, lauric acid, tridecanoic acid, myristic acid, pentadecanoic acid, palmitic acid, margaric acid, stearic acid, nonadecanoic acid, arachic acid, behenic acid, lignoceric acid, cerotic acid, melissic acid, and montanic acid. Also, fatty acid mixtures obtained from the splitting of animal or vegetable fats can also be used herein. It is possible in this way to prepare decanedioic acids of the invention substituted by an ester function.

Alternatively, decanedioic acids according to the invention can also be prepared from dicyclopentadiene and polyalkoxylated fatty alcohols. The fatty alcohols have the formula $R^1OH$, where $R^1$ has the meaning given in (c) above. Preferred are those wherein $R^1$ contains 8 to 18 carbon atoms, including those in the form of their technical mixtures which may be obtained from animal or vegetable fats. These fatty alcohols are used in the form of their ethoxylated and/or propoxylated derivatives, being reacted with 1 to 25 and preferably with 2 to 10 ethylene oxide and/or propylene oxide units. The ethylene oxide and propylene oxide units can have a random or block distribution.

The present invention also relates to a process for the production of the decanedioic acids corresponding to general formula I above wherein dicyclopentadiene is reacted with a compound corresponding to the general formula R—OH, in which R is as defined above, and the bicyclic compound obtained, which corresponds to the following formula

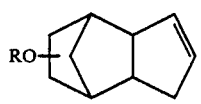
(III)

is cleaved by oxidation at the double bond of the 5-membered ring.

As already discussed, the reaction of dicyclopentadiene with a compound R—OH in the presence of an acid as catalyst is carried out in known manner, cf. U.S. Pat. No. 2,394,582.

The oxidative cleavage of the double bond of the 5-membered ring can be carried out by any of numerous generally known methods, for example by ozonolysis (K. Griesbaum, Brennstoff-Chemie 50, 212 (1969)), by cleavage with permanganate or periodate (Can. J. Chem. 33, 1714 (1955)), by reaction with per acids in the presence of ruthenium trichloride (German Application No. 21 06 307), by reaction with ruthenium oxide, acetaldehyde and oxygen (EP-A 0 021 118), by oxidation with oxygen in the presence of acetaldehyde and compounds of V, Mo, W or Os (U.S. Pat. No. 3.701,804), by reaction with ruthenium tetroxide and sodium hypochlorite (JAOCS 1977, 870A), by reaction of ruthenium trichloride and sodium hypochlorite (Chem. Comm. 21, 1420 (1970)), by reaction with nitric acid and ammonium vanadate (U.S. Pat. No. 2,323,861, GB No. 1,068,905, FR No. 981,609), or by reaction with nitric acid (U.S. Pat. No. 2,265,601).

Cleavage of the double bond with formation of dicarboxylic acids is also possible by preparing the diol by standard methods (F. D. Gunstone, Hydroxylation Methods, Advances in Organic Chemistry, Vol. I, Interscience Publishers, pages 103 et seq., 1960) and cleaving the diol thus prepared to the carboxylic acid, cf. also German Applications Nos. (published) 20 52 815, 21 06 913 (reaction with oxygen, peracetic acid in the presence of cobalt (II) acetate), and German Application (published) 20 35 558 (reaction with peracetic acid in the presence of Ni, Fe, Pd, Mn or Co compounds).

The invention also relates to the use of the bicyclic decanedioic acids corresponding to general formula I above as flotation aids, having particular utility as collectors.

In practice, the compounds of formula I used in accordance with the invention replace the known collectors in known flotation processes for non-sulfidic ores. Accordingly, other reagents commonly used, such as frothers, regulators, activators, deactivators, etc., are also advantageously added to the aqueous suspensions of the ground ores in addition to the collector of the invention. Flotation is carried out under the same conditions as state-of-the-art processes. In this connection, reference is made to the following literature references on technological background of ore preparation: A. Schubert, Aufbereitung fester mineralischer Rohstoffe, Leipzig 1967; B. Wills, Mineral Processing Technology, New York, 1978; D. B. Purchas (ed.) Solid/Liquid Separation Equipment Scale-Up, Croyden 1977; E. S. Perry, C. J. van Oss, E. Grushka (ed.), Separation and Purification Methods, New York, 1973–1978.

The present invention also relates to a process for the separation of non-sulfidic ores by flotation, in which crushed ore is mixed with water to form a suspension, air is introduced into the suspension in the presence of the collector system of the invention and the froth formed is stripped off together with the mineral therein. To obtain economically useful results for the flotation process, the compounds of formula I are used as collectors in quantities of from 50 to 2000 g per metric ton of crude ore, preferably in quantities of from 100 to 1500 g per metric ton of crude ore, in the flotation of nonsulfidic ores.

The compounds of formula I are used with particular advantage in the dressing of ore such as scheelite, baryta, apatite, or iron ores.

The invention is illustrated but not limited by the following Examples.

EXAMPLES

Procedures for the preparation of ethers and esters of dicyclopentadiene (starting material).

The syntheses were carried out in accordance with the teachings of U.S. Pat. Nos. 2,394,582 and 2,395,452.
(A) Reaction product of dicyclopentadiene and lauryl alcohol:

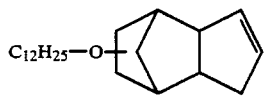

132 g dicyclopentadiene, 186 g lauryl alcohol and 30 g boron fluoride etherate were heated with stirring for 4 hours to approximately 100° C. The reaction mixture was then washed first with hot water, then with sodium carbonate solution and again with water, dried and distilled in vacuo. The desired product distilled over at 185° C./2 mbar in the form of a pale yellow oil.

The reaction products of dicyclopentadiene and 2-ethylhexanol (Bp. 115°–120° C./1 mbar) and ethanol (Bp. 109° C./18 mbar) were obtained by the same method. Reaction products of dicyclopentadiene with stearyl alcohol, isotridecyl alcohol, and an adduct of 3 moles ethylene oxide with a mixture of $C_{12}$–$C_{18}$ fatty alcohols were similarly obtained, but without distillation of the reaction product.

(B)- Reaction product of dicyclopentadiene and acetic acid:

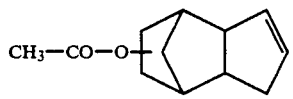

100 g dicyclopentadiene, 250 g acetic acid, 4 g concentrated sulfuric acid and 6 g water were heated with stirring for 5 hours to 70° C. Water was then added with stirring to the reaction mixture. The organic phase was separated off, washed with sodium carbonate solution and with water, dried, and distilled in vacuo. The desired product distilled over in the form of a clear liquid at 95°–100° C./0.1 mbar.

A reaction product of dicyclopentadiene and lauric acid, Bp. 170°–210° C./0.1 mbar, was similarly obtained.

EXAMPLE 1

Dodecyloxy-substituted bicyclic decanedioic acid (I, R = $C_{12}H_{25}$)

The following components were continuously introduced downwards in co-current into a fine steel column (3 m × 40 mm) with a Mellapack filling:
5000 g/hr of a 20% solution of dodecyloxy-dicyclopentadiene obtained by method a) in caprylic acid;
1000 g/hr water which was added to the olefin solution in a static mixer just before entry into the column,
8 m³/hr ozonized air (approx. 160 g ozone/hr, i.e. a 10% excess, based on the olefin).

The reaction enthalpy was dissipated through evaporation of water in the carrier gas stream; the ozonolysis temperature was, stationarily, approximately 36° C. at the column entrance and approximately 20° C. at the exit.

The ozonide solution was separated from the residues of the aqueous phase (approx. 250 g/hr) and worked up without intermediate storage.

Working up was carried out discontinuously. The solution was autocatalytically oxidized for 1.5 hours at 80° C. in an intensively stirred glass or enamelled reactor into which air saturated with steam at 60° C. was introduced (approx. 70 l/hr/kg reaction mixture). 28.5 g 70% hydrogen peroxide solution per kg of reaction mixture were then gradually added dropwise at 80° C. over a period of 2 hours during which the introduction of air was maintained.

In the following after-reaction phase, the contents of the reactor were heated for 30 minutes to 100° C. and then stirred for 1 hour with addition of another 28.5 g $H_2O_2$ (70%) per kg organic phase.

The introduction of air was stopped. The temperature was increased from 100° to 130° C. over a period of about 1 hour with removal of a distillate consisting mainly of water. The final temperature was kept constant at 130° C. until a peroxide value of the organic solution of approximately 10 units had been reached (30 minutes to 1 hr). The fully reacted solution was storable.

The caprylic acid was removed at 2 mbar (heat carrier temperature 165° C.) in a thin-layer evaporator, the residue was taken up in hot glacial acetic acid and crystallized with stirring and cooling. The product was obtained in the form of small ( colorless crystals, Mp. 101°-8° C., acid value 292. More product was obtained by concentration of the mother liquors. Total yield 85%.

EXAMPLE 2

2-Ethylhexyloxy bicyclic decanedioic acid (1, R $CH_3—(CH_2)_3—CH(C_2H_5)—$)

60 g (0.38 mole) $KMnO_4$ were added over a period of 15 minutes at ambient temperature to 39.1 (0.149 mole) 2-ethylhexyl dicyclopentene ether obtained by method A) in 200 ml acetone. After refluxing for 2 hours, the reaction mixture was filtered under suction while still warm and the dicarboxylic acid was washed out from the filter cake, after rinsing with acetone, with a mixture of acetone and water while heat was applied. After acidification and extraction with ether, the filtrates were washed, dried and concentrated.

46% of the highly viscous, dark brown dicarboxylic acid, acid value 312, were obtained, corresponding to 90% of the theoretical value.

The physical data of the compounds of Examples 1 and 2 are shown in Table 1 together with those of other compounds according to the invention.

The compounds according to the invention were tested for their suitability as flotation aids. The flotation tests were carried out at 23° C. in a modified Hallimond tube (microflotation cell) according to B. Dobias, Colloid & Polymer Sci. 259 (1981), pages 775 to 776. The individual tests were each conducted with 2 g ore. Distilled water was used to prepare the pulp. Collector was added to the pulps in such a quantity that 500 g/t collector was present. The conditioning time was 15 minutes in each test. During flotation, an air stream was passed through the pulp at a rate of 4 ml/minute. The flotation time in each test was 2 minutes.

The results of the flotation tests are shown in Table II below. The compounds according to the invention used as collectors are shown in the first column. The total recovery, based on the total quantity of ore, is shown in the second column and the recovery of metal, based on the total quantity of $WO_3$ present in the ore, in the third column. The $WO_3$, CaO and $SiO_2$ contents of the respective concentrates are shown in the fourth to sixth columns. The ore used was an Austrian scheelite ore with the following chemical composition (based on the principal constituents):

| | |
|---|---|
| $WO_3$ | 0.4% |
| CaO | 8.3% |
| $SiO_2$ | 58.2% |
| $Fe_2O_3$ | 7.8% |
| $Al_2O_3$ | 12.5% |
| MgO | 6.9% |

The flotation batch had the following particle size distribution:

| | |
|---|---|
| 30% | <25 m |
| 45% | 25-100 m |
| 24% | 100-200 m |

TABLE 1

| Examples No. | R | Acid value | Physical data |
|---|---|---|---|
| 1 | $C_{12}H_{25}—$ | 292 | Mp. 101–108° C. |
| 2 | $CH_3—(CH_2)_3—CH(C_2H_5)—CH_2$ | 312 | dark yellow oil |
| 3 | $C_2H_5—$ | 403 | brown, glass-like |
| 4 | $C_{18}H_{37}—$ | 237 | Mp. 72–100° C. |
| 5 | isotridecyl— | 240 | dark brown liquid |
| 6 | $C_{12}–C_{18}$ fatty alcohol radical + 3 EO | 191 | dark brown liquid |
| 7 | $CH_3CO—$ | 367 | Mp. 142–174.5° C. |
| 8 | $C_{11}H_{23}CO—$ | 132 | viscous liquid |

TABLE 2

Flotation tests
Austrian scheelite ore, microflotation cell

| Collector Example | Recovery total (%) | Recovery $WO_3$ (%) | Concentrate content (%) | | |
|---|---|---|---|---|---|
| | | | $WO_3$ | CaO | $SiO_2$ |
| 1 | 5.0 | 31 | 2.1 | 16.8 | 44.0 |
| 2 | 1.7 | 14 | 2.6 | 11.1 | 47.7 |
| 3 | 2.0 | 18 | 2.9 | 9.4 | 48.7 |
| 4 | 1.8 | 24 | 4.4 | 11.9 | 44.6 |
| 8 | 3.5 | 37 | 3.6 | 12.7 | 45.4 |
| 6 | 16.5 | 58 | 1.2 | 12.4 | 48.6 |
| 7 | 6.4 | 16 | 0.8 | 9.0 | 49.6 |

As can be seen from the Table, a satisfactory to excellent enrichment of $WO_3$ in the concentrate is obtained by the compounds according to the invention.

We claim:

1. A bicyclic decanedioic acid corresponding to the formula in which R is

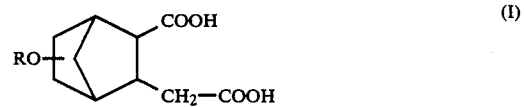

(a) a linear or branched, saturated $C_1$-$C_{22}$ alkyl radical, or (b) a linear or branched, saturated $C_3$-$C_{34}$ alkylcarbonyl radical, or (c) a residue of a polyalkoxylated fatty alcohol corresponding to the formula $$R^1—O—(CH_2—CHR^2—O)_n—CH_2—CHR^2 \quad (II)$$

in which $R^1$ is a saturated $C_2$-$C_{22}$ alkyl group, $R^2$ is hydrogen, methyl, or both, and n is a number of from 0 to 24.

2. The dicarboxylic acid of claim 1 wherein R is a $C_3$-$C_{34}$ alkylcarbonyl radical.

3. A bicyclic decanedioic acid corresponding to the formula

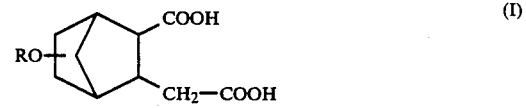

in which R is a linear or branched, saturated $C_1$-$C_{22}$ alkyl radical.

4. The dicarboxylic acid of claim 3 wherein R is a $C_8$–$C_{18}$ alkyl radical.

5. A bicyclic decanedioic acid corresponding to the formula

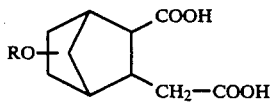 (I)

in which R is a residue of a polyalkyoxylated fatty alcohol corresponding to the formula

 (II)

in which $R^1$ is a saturated $C_2$–$C_{22}$ alkyl group, $R^2$ is hydrogen, methyl, or both, and n is a number of from 0 to 24.

6. The dicarboxylic acid of claim 5 wherein R is an $R^1$—O—$(CH_2$—$CHR^2$—$O)_n$—$CH_2$—$CHR^2$ group in which n is a number of from 1 to 9.

* * * * *